United States Patent
Jung et al.

(10) Patent No.: US 11,589,612 B2
(45) Date of Patent: Feb. 28, 2023

(54) AEROSOL GENERATING DEVICE SUPPLYING POWER TO TWO HEATERS BY USING ONE BATTERY

(71) Applicant: KT&G CORPORATION, Daejeon (KR)

(72) Inventors: Hyung Jin Jung, Seoul (KR); Tae Hun Kim, Yongin-si (KR); Hun Il Lim, Seoul (KR); Jae Sung Choi, Hanam-si (KR); Jung Ho Han, Daejeon (KR)

(73) Assignee: KT&G CORPORATION, Daejeon (KR)

( * ) Notice: Subject to any disclaimer, the term of this patent is extended or adjusted under 35 U.S.C. 154(b) by 270 days.

(21) Appl. No.: 16/955,886

(22) PCT Filed: Nov. 7, 2019

(86) PCT No.: PCT/KR2019/015026
§ 371 (c)(1),
(2) Date: Jun. 19, 2020

(87) PCT Pub. No.: WO2020/101258
PCT Pub. Date: May 22, 2020

(65) Prior Publication Data
US 2021/0068454 A1 Mar. 11, 2021

(30) Foreign Application Priority Data
Nov. 16, 2018 (KR) .......................... 10-2018-0141967

(51) Int. Cl.
*A24F 13/00* (2006.01)
*A24F 40/30* (2020.01)
(Continued)

(52) U.S. Cl.
CPC .............. *A24F 40/30* (2020.01); *A24F 40/10* (2020.01); *A24F 40/20* (2020.01); *A24F 40/46* (2020.01);
(Continued)

(58) Field of Classification Search
CPC ...................................................... A24F 47/00
(Continued)

(56) References Cited

U.S. PATENT DOCUMENTS 9,713,345 B2 7/2017 Farine et al.
9,936,731 B2 4/2018 Hopps
(Continued)

FOREIGN PATENT DOCUMENTS

CN 104254258 A 12/2014
CN 104470386 A 3/2015
(Continued)

OTHER PUBLICATIONS

Extended European Search Report dated Oct. 22, 2021 in European Application No. 19884514.1.
(Continued)

*Primary Examiner* — Phuong K Dinh
(74) *Attorney, Agent, or Firm* — Sughrue Mion, PLLC

(57) ABSTRACT

Provided is an aerosol generating device distributing and transmitting power from a battery to two heaters, wherein the aerosol generating device includes the battery, a first heater heating a first aerosol generating substrate, a second heater heating a second aerosol generating substrate, and a controller controlling power supplied from the battery to the first heater and the second heater, wherein the controller controls power to be supplied from the battery to the first heater and the second heater at different times.

12 Claims, 5 Drawing Sheets

(51) Int. Cl.

| | |
|---|---|
| *A24F 40/65* | (2020.01) |
| *A24F 40/10* | (2020.01) |
| *A24F 40/46* | (2020.01) |
| *A24F 40/20* | (2020.01) |
| *A24F 40/57* | (2020.01) |
| *G05B 19/042* | (2006.01) |
| *H05B 1/02* | (2006.01) |
| *G16H 40/67* | (2018.01) |
| *G16H 40/40* | (2018.01) |

(52) U.S. Cl.
CPC .............. *A24F 40/57* (2020.01); *A24F 40/65* (2020.01); *G05B 19/042* (2013.01); *H05B 1/0297* (2013.01); *G05B 2219/2639* (2013.01); *G16H 40/40* (2018.01); *G16H 40/67* (2018.01)

(58) Field of Classification Search
USPC .................................................. 131/328–329
See application file for complete search history.

(56) References Cited

U.S. PATENT DOCUMENTS

| | | |
|---|---|---|
| 2014/0216485 A1 | 8/2014 | Egoyants et al. |
| 2016/0219938 A1 | 8/2016 | Mamoun et al. |
| 2016/0309784 A1 | 10/2016 | Silverstrini et al. |
| 2016/0374397 A1 | 12/2016 | Jordan et al. |
| 2017/0258138 A1* | 9/2017 | Rostami .................. A24F 40/30 |
| 2018/0125119 A1 | 5/2018 | Cadieux et al. |
| 2018/0220712 A1* | 8/2018 | Hopps .................. A61M 15/06 |
| 2018/0325176 A1 | 11/2018 | Burseg |
| 2019/0053540 A1* | 2/2019 | Baker ..................... A24F 40/60 |
| 2020/0154773 A1 | 5/2020 | Lim et al. |
| 2021/0106051 A1 | 4/2021 | Han et al. |
| 2021/0401059 A1 | 12/2021 | Sebastian et al. |

FOREIGN PATENT DOCUMENTS

| | | |
|---|---|---|
| CN | 104540406 A | 4/2015 |
| CN | 105027016 A | 11/2015 |
| CN | 108135267 A | 6/2018 |
| CN | 108430241 A | 8/2018 |
| CN | 108741237 A | 11/2018 |
| EP | 3 170 413 A1 | 5/2017 |
| JP | 2015-513970 A | 5/2015 |
| KR | 100917902 B1 | 9/2009 |
| KR | 10-2015-0102924 A | 9/2015 |
| KR | 10-1619034 B1 | 5/2016 |
| KR | 10-2016-0098212 A | 8/2016 |
| KR | 10-2018-0111460 A | 10/2018 |
| TW | 201343091 A | 11/2013 |
| WO | 2017/085240 A1 | 5/2017 |
| WO | 2018/182322 A1 | 10/2018 |
| WO | 2018/190589 A2 | 10/2018 |
| WO | 2019/122880 A1 | 6/2019 |

OTHER PUBLICATIONS

Notice of Reasons for Refusal dated Dec. 7, 2021 from the Japanese Patent Office in Japanese Application No. 2020-533268.
Search Report dated Feb. 17, 2020 issued by the Int. Searching Authority in Application No. PCT/KR2019/015026 (PCT/ISA/210).
Written Opinion dated Feb. 17, 2020 issued by the Int. Searching Authority in Application No. PCT/KR2019/015026 (PCT/ISA/237).
Communication dated Jan. 28, 2021 by the Taiwanese Patent Office in application No. 108141691.
Notification of Reason for Refusal dated May 29, 2020 from the Korean Intellectual Property Office in KR Application No. 10-2018-0141967.
Notice of Reasons for Refusal dated Jun. 29, 2021 by the Japanese Patent Office in Japanese Application No. 2020-533268.
Communication dated Jul. 9, 2021 by the Taiwanese Patent Office in Taiwanese Application No. 108141691.
Office Action dated Oct. 10, 2022 in Chinese Application No. 201980006528.0.

* cited by examiner

AEROSOL GENERATING DEVICE SUPPLYING POWER TO TWO HEATERS BY USING ONE BATTERY

TECHNICAL FIELD

The present disclosure relates to an aerosol generating device, and more particularly, to an aerosol generating device distributing and transmitting power from one battery to two heaters.

BACKGROUND ART

Recently, the demand for alternative methods to overcome the shortcomings of general cigarettes has increased. For example, there is growing demand for a method of generating aerosol by heating an aerosol generating material in cigarettes, rather than by combusting cigarettes. Accordingly, studies on a heating-type cigarette or a heating-type aerosol generating device have been actively conducted.

An aerosol generating device may include two heaters. One heater may be used to heat a cigarette including nicotine, and the other one heater may be used to heat a cartridge including a liquid substrate. Also, the aerosol generating device may include a battery to be used while moving.

Since the battery has limited power, when power is supplied to satisfy all of power needed by two heaters, the aerosol generating device may malfunction due to an instantaneous voltage drop or the like. Therefore, studies have been conducted to properly distribute and transmit power from a battery to two heaters.

DESCRIPTION OF EMBODIMENTS

Technical Problem

Provided is a method of distributing and transmitting power to two heaters within a range of power which may be output from a battery. Provided is also an aerosol generating device operating according to the method described above. The technical problems to be solved are not limited to the technical problems as described above, and other technical problems may exist.

Solution to Problem

According to an aspect of the present disclosure, an aerosol generating device may include: a battery; a first heater heating a first aerosol generating substrate; a second heater heating a second aerosol generating substrate; and a controller controlling power supplied from the battery to the first heater and the second heater, wherein the controller controls power to be supplied from the battery to the first heater and the second heater at different times.

Advantageous Effects of Disclosure

A controller may control a time when power is transmitted from a battery to a first heater not to overlap a time when power is transmitted from the battery to a second heater to prevent a voltage output from the battery from dropping and prevent a malfunction of an aerosol generating device or an occurrence of a device defect.

Also, the controller may operate in a plurality of control modes, and the plurality of control modes may include a first control mode controlling power to be first transmitted to the first heater and a second control mode controlling power to be first transmitted to the second heater. The first control mode is a mode in which a cigarette is normally heated according to a preset temperature profile to provide a user with a preferred taste, and the second mode is a mode in which a cartridge is normally heated according to a preset temperature profile to provide the user with a preferred amount of aerosol. Users may have a priority between a smoking taste and an amount of aerosol according to likings of the users. A user may select one control mode from a plurality of control modes and use an aerosol generating device according to a liking of the user.

The effects of the present disclosure are not limited by the examples described above, and more various effects are included in the present disclosure.

BEST MODE

Figure 1:
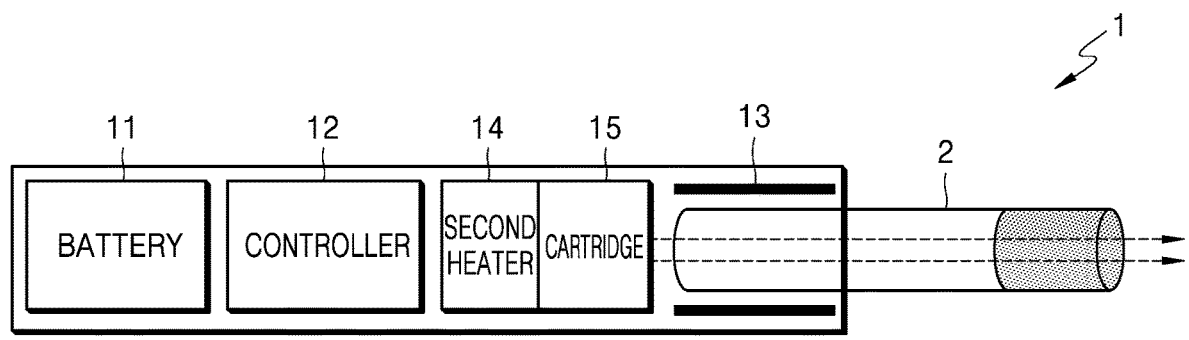
FIGS. 1 and 2 are diagrams showing examples in which a cigarette is inserted into an aerosol generating device.

According to an aspect of the present disclosure, an aerosol generating device may include: a battery; a first heater heating a first aerosol generating substrate; a second heater heating a second aerosol generating substrate; and a controller controlling power supplied from the battery to the first heater and the second heater, wherein the controller controls power to be supplied from the battery to the first heater and the second heater at different times.

The controller may include a plurality of control modes for controlling power supplied from the battery to the first heater and the second heater according to priorities of the first heater and the second heater.

The plurality of control modes may include: a first control mode for controlling power to be first supplied to the first heater; and a second control mode for controlling power to be first transmitted to the second heater.

The controller may control power supplied from the battery to the first heater and the second heater according to one control mode among the plurality of control modes, wherein the one control mode is determined by a user command.

The aerosol generating device may further include a communicator performing communication with an external device, wherein the user command is input to the external device and received through the communicator.

The controller may acquire a first duty cycle which is a duty cycle of power needed by the first heater for a current control period and a second duty cycle which is a duty cycle of power needed by the second heater in the current control period.

The controller may control power satisfying the first duty cycle to be supplied from the battery to the first heater during a first period in the current control period and control power to be supplied from the battery to the second heater during at least some of a remaining period in the current control period.

The controller may control power satisfying the second duty cycle to be supplied from the battery to the second heater during a second period in the current control period and control power to be supplied from the battery to the first heater during at least some of a remaining period in the current control period.

The controller may control power supplied from the battery to the first heater in the current control period and at least one subsequent control period such that a total amount of power supplied from the battery to the first heater satisfies the first duty cycle.

The controller may output a pulse width modulation signal to control power supplied from the battery to the first heater and the second heater.

The first aerosol generating substrate may be a solid substrate comprising nicotine, and the second aerosol generating substrate may be a liquid substrate comprising an aerosol forming substance.

A sum of the first duty cycle and the second duty cycle may exceed 100%.

According to another aspect of the present disclosure, a method of controlling an aerosol generating device, may include: acquiring a first duty cycle which is a duty cycle of power needed by a first heater included in the aerosol generating device and a second duty cycle which is a duty cycle of power needed by a second heater included in the aerosol generating device; checking a control mode for controlling power supplied to the first heater and the second heater; and controlling power supplied from a battery to the first heater and the second heater according to the checked control mode, wherein power is supplied from the battery to the first heater and the second heater at different times.

The method may further include determining priorities of the first heater and the second heater, wherein the power is first supplied to the heater having the higher priority among the first heater and the second heater.

MODE OF DISCLOSURE

With respect to the terms used to describe the various embodiments, general terms which are currently and widely used are selected in consideration of functions of structural elements in the various embodiments of the present disclosure. However, meanings of the terms can be changed according to intention, a judicial precedence, the appearance of new technology, and the like. In addition, in certain cases, a term which is not commonly used can be selected. In such a case, the meaning of the term will be described in detail at the corresponding portion in the description of the present disclosure. Therefore, the terms used in the various embodiments of the present disclosure should be defined based on the meanings of the terms and the descriptions provided herein.

In addition, unless explicitly described to the contrary, the word "comprise" and variations such as "comprises" or "comprising" will be understood to imply the inclusion of stated elements but not the exclusion of any other elements. In addition, the terms "-er", "-or", and "module" described in the specification mean units for processing at least one function and/or operation and can be implemented by hardware components or software components and combinations thereof.

Hereinafter, the present disclosure will now be described more fully with reference to the accompanying drawings, in which exemplary embodiments of the present disclosure are shown such that one of ordinary skill in the art may easily work the present disclosure. The disclosure may, however, be embodied in many different forms and should not be construed as being limited to the embodiments set forth herein.

Hereinafter, embodiments of the present disclosure will be described in detail with reference to the drawings.

Figure 2:
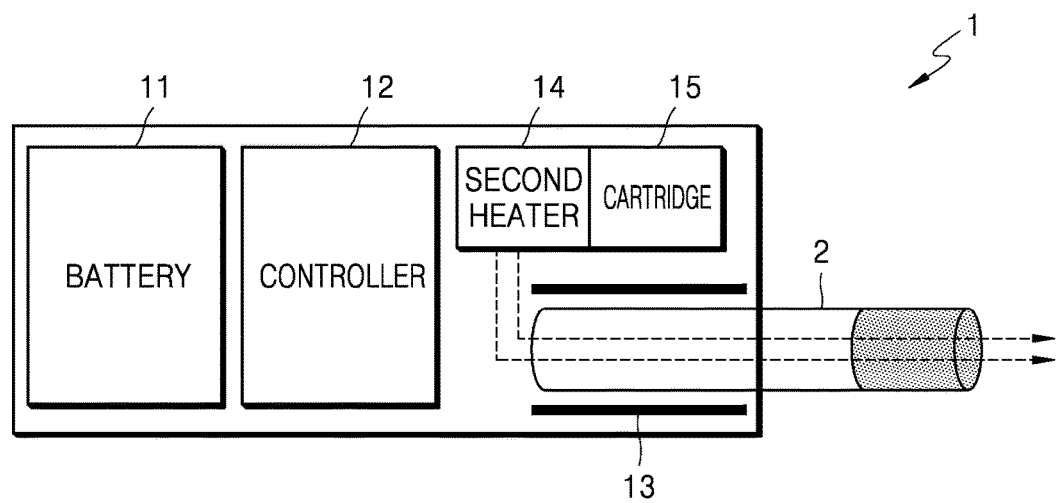

FIGS. 1 and 2 are diagrams showing examples in which a cigarette is inserted into an aerosol generating device.

Referring to FIGS. 1 and 2, an aerosol generating device 1 includes a battery 11, a controller 12, a first heater 13, a second heater 14, and a cartridge 15. Also, a cigarette 2 may be inserted into an internal space of the aerosol generating device 1.

FIGS. 1 and 2 illustrate only components of the aerosol generating device 1, which are related to the present embodiment. Therefore, it will be understood by one of ordinary skill in the art related to the present embodiment that other general-purpose components may be further included in the aerosol generating device 1, in addition to the components illustrated in FIGS. 1 and 2.

FIG. 1 illustrates that the battery 11, the controller 12, the first heater 13, the second hearer 14, and the cartridge 15 are arranged in a line. Also, FIG. 2 illustrates that the first heater 13 and the second heater 14 are arranged in parallel, and the second heater 14 and the cartridge 15 are arranged in a line. However, the internal structure of the aerosol generating device 1 is not limited to the structures illustrated in FIGS. 1 and 2. In other words, according to a design of the aerosol generating device 1, the arrangement of the battery 11, the controller 12, the first heater 13, the second heater 14, and the cartridge 15 may be changed.

When the cigarette 2 is inserted into the aerosol generating device 1, the aerosol generating device 1 may operate the first heater 13 and/or the second heater 14 to generate aerosol. The aerosol generated by the first heater 13 and/or the second heater 14 is delivered to the user by passing through the cigarette 2.

As needed, even when the cigarette 2 is not inserted into the aerosol generating device 1, the aerosol generating device 1 may heat the first heater 13 and the second heater 14.

The battery 11 may supply power to be used for the aerosol generating device 1 to operate. For example, the battery 11 may supply power to heat the first heater 13 or the second heater 14 and may supply power for operating the controller 12. Also, the battery 11 may supply power for operations of a display, a sensor, a motor, etc. mounted in the aerosol generating device 1.

For example, an output voltage of the battery 11 may be in a range of 4.0 V to 5.0 V, and a capacity of the battery 11 may be in a range of 2000 mAh to 4000 mAh. Preferably, but not necessarily, the output voltage of the battery 11 may be 4.2 V, and the capacity of the battery 11 may be 3000 mAh, but the output voltage of the battery 11 is not limited thereto.

The controller 12 may control overall operations of the aerosol generating device 1. In detail, the controller 12 may control not only operations of the battery 11, the first heater 13, and the second heater 14, but also operations of other components included in the aerosol generating device 1. Also, the controller 12 may check a state of each of the components of the aerosol generating device 1 to determine whether or not the aerosol generating device 1 is able to operate.

The controller 12 may include at least one processor. A processor can be implemented as an array of a plurality of logic gates or can be implemented as a combination of a general-purpose microprocessor and a memory in which a program executable in the microprocessor is stored. It will be understood by one of ordinary skill in the art that the processor can be implemented in other forms of hardware.

The first heater 13 may be heated by the power supplied from the battery 11. For example, when the cigarette is inserted into the aerosol generating device 1, the first heater 13 may be located outside the cigarette. Thus, the heated first heater 13 may increase a temperature of an aerosol generating material in the cigarette.

The first heater 13 may be an electro-resistive heater. For example, the first heater 13 may include an electrically insulating substrate (e.g., a substrate formed of polyimide) and an electrically conductive track, and the first heater 13 may be heated when currents flow along the electrically conductive track. However, the first heater 13 is not limited to the example described above and may include all heaters which may be heated to a desired temperature. Here, the desired temperature may be preset in the aerosol generating device 1 or may be set by a user.

As another example, the first heater 13 may include an induction heater. In detail, the first heater 13 may include an electrically conductive coil for heating a cigarette in an induction heating method, and the cigarette may include a susceptor which may be heated by the induction heater.

For example, the first heater 13 may include a tube-type heating element, a plate-type heating element, a needle-type heating element, or a rod-type heating element, and may heat the inside or the outside of the cigarette 2, according to the shape of the heating element.

Also, the aerosol generating device 1 may include a plurality of first heaters 13. Here, the plurality of first heaters 13 may be inserted into the cigarette 2 or may be arranged outside the cigarette 2. Also, some of the plurality of first heaters 13 may be inserted into the cigarette 2, and the others may be arranged outside the cigarette 2. In addition, the shape of the first heater 13 is not limited to the shapes illustrated in FIGS. 1 and 2 and may include various shapes.

The second heater 14 may generate aerosol by heating a liquid composition (a second aerosol generating substrate) included in the cartridge 15, and the generated aerosol may pass through the cigarette 2 to be delivered to the user. In other words, the aerosol heated and generated by the second heater 14 may move along an air flow passage of the aerosol generating device 1, and the air flow passage may be configured such that the aerosol generated by the second heater 14 passes through the cigarette to be delivered to the user.

For example, the cartridge 15 may include a liquid storage and a liquid delivery element, but it is not limited thereto. For example, the second heater 14 and the cartridge 15 may be included in the aerosol generating device 1 as independent modules.

The liquid storage may store a liquid composition. For example, the liquid composition may be a liquid including a tobacco-containing material having a volatile tobacco flavor component, or a liquid including a non-tobacco material. The cartridge 15 may be formed to be attached to and detached from the second heater 14 or may be formed integrally with the second heater 14.

For example, the liquid composition may include water, a solvent, ethanol, plant extract, spices, flavorings, or a vitamin mixture. The spices may include menthol, peppermint, spearmint oil, and various fruit-flavored ingredients, but are not limited thereto. The flavorings may include ingredients capable of providing various flavors or tastes to a user. Vitamin mixtures may be a mixture of at least one of vitamin A, vitamin B, vitamin C, and vitamin E, but are not limited thereto. Also, the liquid composition may include an aerosol forming substance, such as glycerin and propylene glycol.

The liquid delivery element may deliver the liquid composition of the liquid storage to the second heater. For example, the liquid delivery element may be a wick such as cotton fiber, ceramic fiber, glass fiber, or porous ceramic, but is not limited thereto.

The second heater 14 heats the liquid composition delivered by the liquid delivery element. For example, the second heater 14 may be a metal heating wire, a metal hot plate, a ceramic heater, or the like, but is not limited thereto. In addition, the second heater 14 may include a conductive filament such as nichrome wire and may be positioned as being wound around the liquid delivery element. The second heater 14 may be heated by a current supply and may transfer heat to the liquid composition in contact with the heating element, thereby heating the liquid composition. As a result, aerosol may be generated.

For example, the second heater 14 and the cartridge 15 may be referred to as a cartomizer or an atomizer, but it is not limited thereto.

The aerosol generating device 1 may further include general-purpose components in addition to the battery 11, the controller 12, the first heater 13, the second heater 14, and the cartridge 15. For example, the aerosol generating device 1 may include a display capable of outputting visual information and/or a motor for outputting haptic information. Also, the aerosol generating device 1 may include at least one sensor (a puff detecting sensor, a temperature detecting sensor, a cigarette insertion detecting sensor, etc.). Also, the aerosol generating device 1 may be formed as a structure where, even when the cigarette 2 is inserted into the aerosol generating device 1, external air may be introduced or internal air may be discharged.

Although not illustrated in FIGS. 1 and 2, the aerosol generating device 1 and an additional cradle may form together a system. For example, the cradle may be used to charge the battery 11 of the aerosol generating device 1. Alternatively, the first heater 13 may be heated when the cradle and the aerosol generating device 1 are coupled to each other.

Also, although not illustrated in FIGS. 1 and 2, the aerosol generating device 1 may include a communicator for performing communication with an external device. The aerosol generating device 1 may perform wireless communication or wired communication (e.g., an Ethernet communication or USB communication method, or the like) with the external device through the communicator. For example, communication methods, such as a wireless local area network (WLAN), Bluetooth, ZigBee, Infrared Data Association (IrDA), and Radio-Frequency Identification (RFID), may be used for the wireless communication between the aerosol generating device 1 and the external device.

The cigarette 2 may be similar as a general combustive cigarette. For example, the cigarette 2 may be divided into a first portion including an aerosol generating material and a second portion including a filter, etc. Alternatively, the second portion of the cigarette 2 may also include an aerosol generating material. For example, an aerosol generating material made in the form of granules or capsules may be inserted into the second portion.

The first portion may be entirely inserted into the aerosol generating device 1, and the second portion may be exposed to the outside. Alternatively, only a portion of the first portion may be inserted into the aerosol generating device 1. Otherwise, the entire first portion and a portion of the second portion may be inserted into the aerosol generating device 1. The user may puff aerosol while holding the second portion by the mouth of the user. In this case, the aerosol is generated by external air passing through the first portion, and the generated aerosol passes through the second portion and is delivered to the user's mouth.

For example, the external air may flow into at least one air passage formed in the aerosol generating device 1. For example, opening and closing of the air passage and/or a size of the air passage formed in the aerosol generating device 1 may be controlled by the user. Accordingly, the amount and smoothness of the vapor may be adjusted by the user. As another example, the external air may flow into the cigarette 2 through at least one hole formed in a surface of the cigarette 2.

Hereinafter, an example of the cigarette 2 will be described with reference to FIG. 3.

Figure 3:
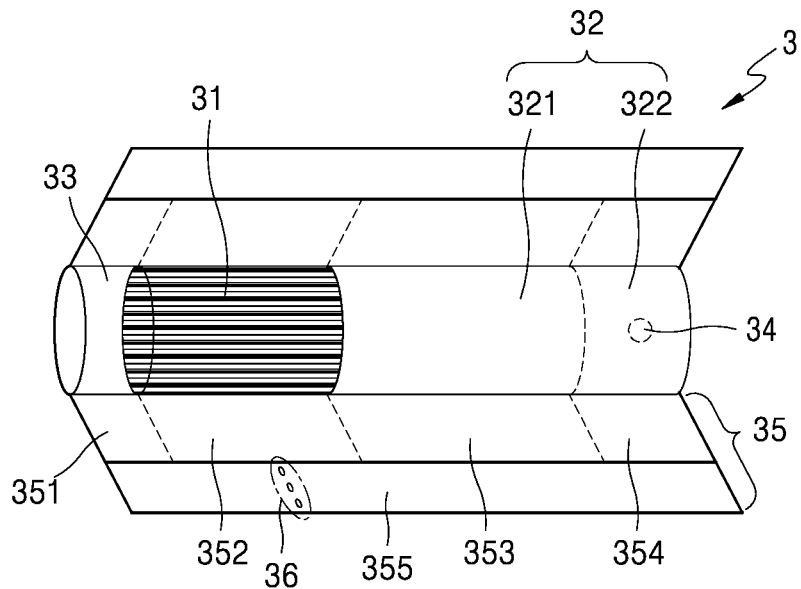
FIG. 3 is a drawing illustrating an example of a cigarette.

FIG. 3 is a drawing illustrating an example of a cigarette.

Referring to FIG. 3, a cigarette 3 includes a tobacco rod 31, a filter rod 32, and a front-end plug 33. The first portion described above with reference to FIGS. 1 and 2 includes the tobacco rod 31 and the front-end plug 33, and the second portion described above with reference to FIGS. 1 and 2 includes the filter rod 32.

For example, a length of the front-end plug 33 may be about 7 mm, a length of the tobacco rod 31 may be about 15 mm, a length of a first segment 321 may be about 12 mm, and a length of a second segment 322 may be about 14 mm. However, embodiments are not limited thereto.

The tobacco rod 31 may include an aerosol generating material (first aerosol generating material)). For example, the aerosol generating material may include at least one of glycerin, propylene glycol, ethylene glycol, dipropylene glycol, diethylene glycol, triethylene glycol, tetraethylene glycol, and oleyl alcohol, but it is not limited thereto. Also, the tobacco rod 31 may include other additives, such as flavors, a wetting agent, and/or organic acid. Also, the tobacco rod 31 may include a flavored liquid, such as menthol or a moisturizer, which is injected to the tobacco rod 31.

The tobacco rod 31 may be manufactured in various forms. For example, the tobacco rod 31 may be formed as a sheet or a strand. Also, the tobacco rod 31 may be formed as a pipe tobacco, which is formed of tiny bits cut from a tobacco sheet. Also, the tobacco rod 31 may be surrounded by a heat conductive material. For example, the heat-conducting material may be, but is not limited to, a metal foil such as aluminum foil. For example, the heat conductive material surrounding the tobacco rod 31 may uniformly distribute heat transmitted to the tobacco rod 31, and thus, the heat conductivity of the tobacco rod may be increased and taste of the tobacco may be improved. Also, the heat conductive material surrounding the tobacco rod 31 may function as a susceptor heated by the induction heater. Here, although not illustrated in the drawings, the tobacco rod 31 may further include an additional susceptor, in addition to the heat conductive material surrounding the tobacco rod 31.

The filter rod 32 may include the first segment 321 and the second segment 322.

The first segment 321 may be a cellulous acetate filter. For example, the first segment 321 may be a tube-type structure including a hollow inside. A cooling effect of an aerosol may be generated by the first segment 321. A diameter of the hollow included in the first segment 321 may be an appropriate diameter within a range of 2 mm to 4.5 mm but is not limited thereto.

The length of the first segment 321 may be within a range of 4 mm to 30 mm but is not limited thereto. Preferably, the length of the first segment 321 may be 12 mm but is not limited thereto.

The hardness of the first segment 321 may be adjusted by adjusting the content of a plasticizer when the first segment 321 is manufactured. Also, the first segment 321 may be manufactured by inserting a structure, such as a film or tube of the same or different material, into an inside thereof (e.g., the hollow).

The second segment 322 may be a cellulous acetate filter. The length of the second segment 322 may be within a range of 4 mm to 20 mm. For example, the length of the second segment 322 may be about 14 mm but is not limited thereto.

Also, the second segment 322 may include at least one capsule 34. Here, the capsule 34 may generate a flavor or an aerosol. For example, the capsule 34 may have a configuration in which a liquid containing a flavoring material is wrapped with a film. For example, the capsule 34 may have a spherical or cylindrical shape, but is not limited thereto.

The front-end plug 33 may prevent the tobacco rod 31 from being detached and prevent liquefied aerosol from flowing into the aerosol generating device 1 of FIGS. 1 through 3 from the tobacco rod 31, during smoking.

The cigarette 3 may be packaged using at least one wrapper 35. The wrapper 35 may have at least one hole through which external air may be introduced or internal air may be discharged. For example, the front-end plug 33 may be packaged using a first wrapper 351, the tobacco rod 31 may be packaged using a second wrapper 352, the first segment 321 may be packaged using a third wrapper 353, and the second segment 322 may be packaged using a fourth wrapper 354. Also, the entire cigarette 3 may be re-packaged using a fifth wrapper 355.

In addition, at least one perforation 36 may be formed in the fifth wrapper 355. For example, the perforation 36 may be formed in an area of the fifth wrapper 355 surrounding the tobacco rod 31 but is not limited thereto. The perforation 36 may transfer heat formed by the first heater 13 illustrated in FIGS. 1 and 2 to the inside of the tobacco rod 31.

As in the description with reference to FIGS. 1 and 2, the aerosol generating device 1 includes the battery 11 and two heaters 13 and 14, power is transmitted from the battery 11 to the first heater 13 to heat the cigarette 2, and power is transmitted from the battery 11 to the second heater 14 to heat the liquid composition.

Since the capacity of the battery 11 is limited, when power is supplied to satisfy all of power needed by the first heater 13 and the second heater 14, an instantaneous voltage drop may occur, and thus, the malfunction of the aerosol generating device 1 or the device detect may occur.

To prevent this, in the present disclosure, the controller 12 controls power to be supplied from the battery 11 to the first heater 13 and the second heater 14 at different times. Hereafter, a method in which the controller 12 controls power supplied to the first heater 13 and the second heater 14 in consideration of limited power of the battery 11 will be described.

Figure 4:
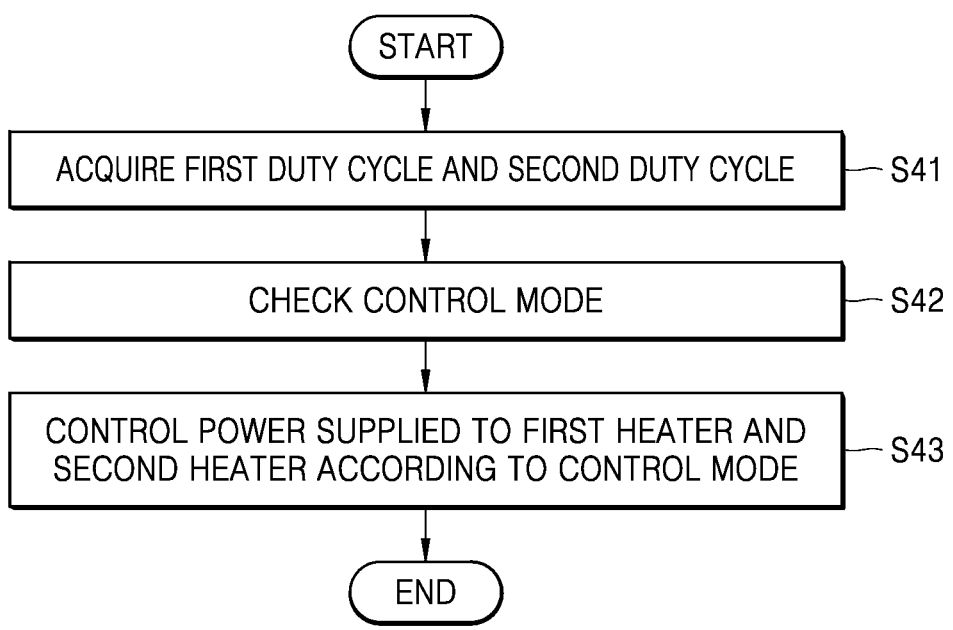
FIG. 4 is a flowchart illustrating an example of a method in which a controller controls power transmitted to heaters.

FIG. 4 is a flowchart illustrating an example of a method in which a controller controls power transmitted to heaters.

On the basis of the structures of the aerosol generating device 1 illustrated in FIGS. 1 and 2, the control method illustrated in FIG. 4 will be described.

In operation S41, the controller 12 acquires, for a current control period, a first duty cycle which is a duty cycle of power needed by the first heater 13 and a second duty cycle which is a duty cycle of power needed by the second heater 14.

The controller 12 may use a pulse width modulation control method to control power supplied from the battery 11 to the first heater 13 and the second heater 14. One control period of the controller 12 may be in a range of 100 μs to 1000 μs. Preferably, the one control period may be 500 μs. The current control period refers to one control period corresponding to a current time point at which control is to be performed, among a plurality of control periods.

Figure 5:
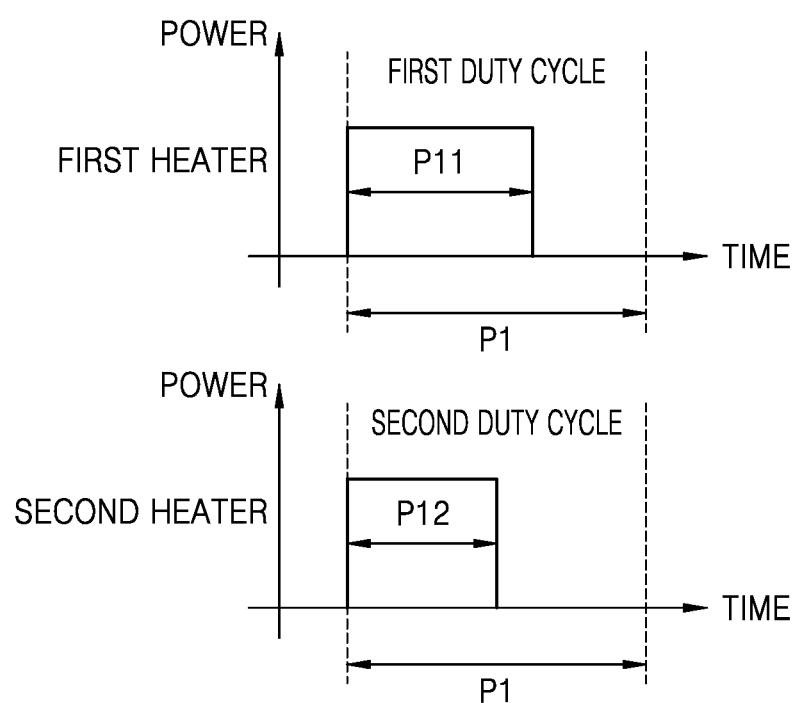
FIG. 5 is a view illustrating an example of power needed by a first heater and power needed by a second heater for a current control period.

FIG. 5 is a view illustrating an example of power needed by a first heater and power needed by a second heater for a current control period.

Referring to FIGS. 4 and 5, a first duty cycle may be acquired by a ratio of a period P11, in which power is to be supplied to the first heater 13, to a current control period P1. Similarly, a second duty cycle may be acquired by a ratio of a period P12, in which power is to be supplied to the second heater 14, to the current control period P1.

The first duty cycle may be determined according to a temperature at which the first heater 13 heats a cigarette. For example, in a case where a temperature profile of the first heater 13 is set such that a temperature is lowered according to the progress of smoking, the first duty cycle may have a value that decreases as smoking progresses. Here, the temperature profile of the first heater 13 refers to a preset temperature profile for heating the first heater 13.

Similarly, the second duty cycle may be determined according to a temperature at which the second heater 14 heats the cartridge 15 and may change according to a temperature profile of the second heater 14. Here, the temperature profile of the second heater 14 refers to a preset temperature profile for heating the second heater 14.

In other words, since the first duty cycle and the second duty cycle may respectively change according to the temperature profile of the first heater 13 and the temperature profile of the second heater 14, the controller 12 may acquire the first duty cycle and the second duty cycle at every control period or every particular control period.

If a sum of the period P11 in which power is to be supplied to the first heater 13 and the period P12 in which power is to be supplied to the second heater 14 exceeds the current control period P1, i.e., a sum of the first duty cycle and the second duty cycle exceeds 100%, it is difficult that limited power of the battery 11 provides the first heater 13 and the second heater 14 with power satisfying the first duty cycle and the second duty cycle in the current control period P1.

The controller 12 may control power transmitted to the first heater 13 and the second heater 14 according to a control mode in consideration of the limited power of the battery 11, and such power control may be performed in operations S42 and S43 illustrated in FIG. 4.

Referring to FIG. 4 again, in operation S42, the controller 12 identifies a control mode to be applied to the current control period, among a plurality of control modes.

The plurality of control modes may be distinguished according to priorities of the first heater 13 and the second heater 14 and may include a first control mode and a second control mode.

In the first control mode, the first heater 13 may have a priority and power is first transmitted from the battery 11 to the first heater 13. In other words, the first control mode is a mode in which power is distributed to first satisfy power needed by the first heater 13 in distributing power of the battery 11 having limited power. In the first control mode, the cigarette 2 may be normally heated according to a temperature profile of the first heater 13, and the user may be provided with a desired smoking taste.

In the second control mode, the second heater 14 has a priority and power is first transmitted from the battery 11 to the second heater 14. In other words, the second control mode is a mode in which power is distributed to first satisfy power needed by the second heater 14 in distributing power of the battery 11 having the limited power. In the second control mode, the cartridge 15 may be normally heated according to a temperature profile of the second heater 14, and the user may be provided with a desired amount of aerosol.

The user may select a control mode in which the controller 12 may operate, from the plurality of control modes. In other words, the controller 12 may identify a control mode selected by the user and perform control in the control mode.

The user may select a control mode through an external device, and the selected control mode may be received through the communicator of the aerosol generating device 1 and transmitted to the controller 12.

The external device used for the user to select the control mode may include a smart phone, a tablet computer, a personal computer (PC), a personal digital assistant (PDA), a wearable device, and the like but is not limited to the listed types.

The user may select a control mode before starting smoking or while smoking.

As an example, the user may select one control mode from the first control mode and the second control mode for each smoking. Here, a "smoking" refers to one cycle including a plurality of puffs. In other words, the user may select one control mode from the first control mode and the second control mode before starting smoking and then start smoking.

As another example, the user may select one of the first control mode and the second control mode as a default control mode and change the default mode to another control mode before starting smoking or while smoking.

As another example, the user may select a plurality of control modes for one smoking. For example, the user may select the first control mode for the first puff to the third puff and the second control mode for subsequent puffs in one smoking.

For example, the first control mode may be a mode in which a cigarette is normally heated according to a preset temperature profile to thereby provide the user with a desired smoking taste. The second control mode may be a mode in which a cartridge is normally heated according to a preset temperature profile to thereby provide the user with a desired amount of aerosol. According to users, likings may be different, such as a liking for smoking taste or a liking for a sufficient amount of aerosol. The user may select one control mode from a plurality of control modes to use an aerosol generating device according to the user's liking.

In operation S43, the controller 12 controls power to be transmitted from the battery 11 to the first heater 13 and the second heater 14 according to an acquired control mode.

Hereinafter, an example in which the controller 12 controls power transmitted to heaters 13, 14 according to a first control mode will be described with reference to FIG. 6. Also, an example in which the controller 12 controls power transmitted to heaters 13, 14 according to a second control mode will be described with reference to FIG. 7.

Figure 6:
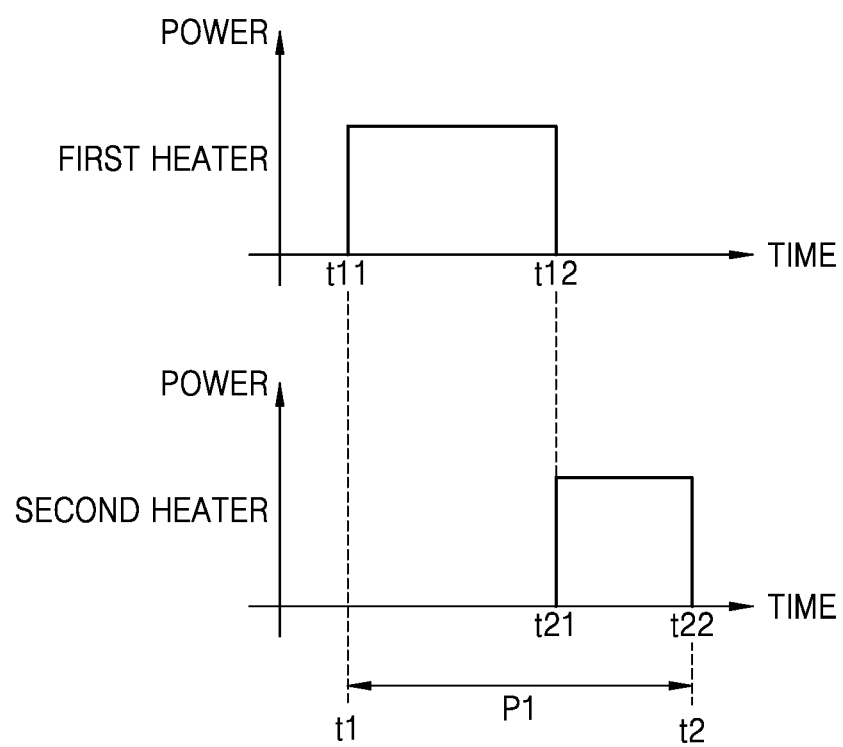
FIG. 6 is a view illustrating an example of power supplied from a battery to a first heater and a second heater according to a first control mode.

FIG. 6 is a view illustrating an example of power supplied from a battery to a first heater and a second heater according to a first control mode.

In a current control period P1 having a period from t1 to t2, the controller 12 controls power corresponding to a first duty cycle, which is a duty cycle of power needed by the first heater 13, to be transmitted to the first heater 13 during a period from t11 to t12 and controls power to be transmitted to the second heater 14 during a remaining period from t12 to t2.

In some cases, a sum of the first duty cycle and a second duty cycle may exceed 100%. In this case, even if power is transmitted to the second heater 14 during the remaining period from t12 to t2 after the power is transmitted to the first heater 13, the power transmitted to the second heater 14 may not satisfy the second duty cycle.

However, assuming that the second heater 14 is continuously heated for a short time period, such as 1 seconds to about 2 seconds, similar to a time period during which the user puffs aerosol, an amount of aerosol generate by supplying normal power to the second heater 14 may not be significantly different from an amount of aerosol generated by supplying insufficient power to the second heater 14. Therefore, in a first control mode, although power is insufficiently supplied to the second heater 14 in a current control period, the second heater 14 may not be compensated for insufficient power.

For example, when the first duty cycle is 60%, the second duty cycle is 50%, power is transmitted to the first heater 13 during the period from t11 to t12 corresponding to a duty cycle of 60% for the current control period P1 according to the first control mode. In this case, even if power is transmitted to the second heater 14 in the remaining period from t12 to t2, a duty cycle of the power supplied to the second heater 14 is 40%. As a result, in the current control period P1, the second heater 14 may be supplied with power which is insufficient by 10% duty cycle and may not be compensated for power corresponding to 10% duty cycle.

FIG. 6 illustrates that a start time point t1 of the current control period P1 and a time point t11 when power starts to be supplied to the first heater 13 are indicated as the same time point, but the time point t11 may be a time point after the start time point t1. Similarly, a time point t21 when power starts to be supplied to the second heater 14 may be a time point after a time point t12 when a power supply to the first heater 13 ends, and an end time point t2 of the current control period P1 may be a time point after a time point t22 when power supply to the second heater 14 ends.

Also, FIG. 6 illustrates that the period from t11 to t12 precedes a period from t21 to t22, but the period from t21 to t22 may precede the period from t11 to t12. In other words, after power is temporally first supplied to the second heater 14, power satisfying the first duty cycle may be supplied to the first heater 13.

As described above, the controller 11 may control power to be transmitted to the first heater 13 and the second heater 14 at different times such that power may be stably supplied from the battery 11 having a limited capacity to the first heater 13 and the second heater 14. Also, power satisfying the first duty cycle may be supplied to the first heater 13 such that the cigarette 2 may be heated according to a temperature profile of the first heater 13 and a smoking taste desired by the user may be provided.

Figure 7:
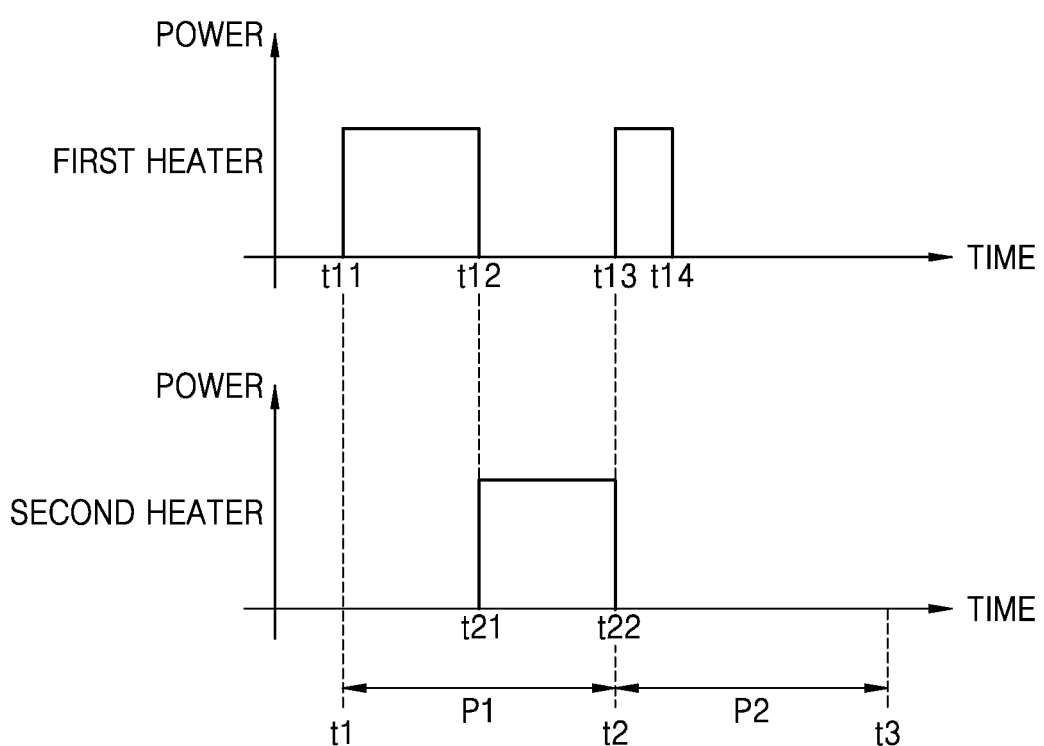
FIG. 7 is a view illustrating an example of power supplied from a battery to a first heater and a second heater according to a second control mode.

FIG. 7 is a view illustrating an example of power supplied from a battery to a first heater and a second heater according to a second control mode.

In a current control period P1 having a period from t1 to t2, the controller 12 controls power corresponding to a second duty cycle, which is a duty cycle of power needed by the second heater 14, to be transmitted to the second heater 14 during a period from t21 to t22 and controls power to transmitted to the first heater 13 during a remaining period from t1 to t21.

In some cases, a sum of a first duty cycle and the second duty cycle may exceed 100%. In this case, even if power is controlled to be transmitted to the first heater 13 in all of the remaining period from t1 to t21, the power supplied to the first heater 13 may not satisfy the first duty cycle.

Since the first heater 13 may continuously heat the cigarette 2 during the entire smoking period, when sufficient power is not continuously supplied to the first heater 13, the cigarette 2 may not be heated according to a temperature profile of the first heater 13.

To prevent this, the controller 12 may control the deficit of power for the first heater 13 in the current control period P1 to be compensated for and supplied to the first heater 13 in a next control period P2.

For example, assuming that the first duty cycle is 60%, the second duty cycle is 50%, and power is transmitted to the second heater 14 during a period from t21 to t22 corresponding to a duty cycle of 50% for the current control period P1 according to a second control mode, even if power is transmitted to the first heater 13 in the remaining period from t1 to t21, a duty cycle of the power supplied to the first heater 13 is 50%. In other words, since a duty cycle of power needed by the first heater 13 is 60% and a duty cycle of supplied power is 50%, the first heater 13 is supplied with power that is insufficient by a duty cycle of 10%. The controller 12 may compensate the first heater 13 for insufficient power by controlling power to be transmitted to the first heater 13 during a period from t13 to t14 corresponding to the duty cycle of 10% in the next control period P2.

In some cases, the next control period P2 may have no extra period to compensate the first heater 13 for power. In this case, the controller 12 may control insufficient power to be supplied to the first heater 13 in control periods subsequent to the next control period P2.

As described above, the controller 12 may control a total sum of duty profiles of power supplied to the first heater 13 in the current control period P1 and the subsequent control periods to satisfy a first duty profile such that power not supplied in the current control mode P1 may be compensated for and transmitted to the first heater 13.

FIG. 7 illustrates that a start time point t1 of the current control period P1 and a time point t11 when power starts to be supplied to the first heater 13 indicate the same time point, but the time point t11 may be a time point after the start time point t1. Similarly, a time t21 when power starts to be supplied to the second heater 14 may be a time point after a time point t12 when a power supply to the first heater 13 ends, and an end time point t2 of the current control period P1 may be a time point after a time point t22 when a power supply to the second heater 14 ends. Similarly, a time point t13 when compensated power starts to be supplied to the first heater 13 may be a time point after a start time point t2 of the next control period P2.

Also, FIG. 7 illustrates that a period from t11 to t12 precedes the period from t21 to t22, but the period from t21 to t22 may precede the period from t11 to t12. In other words, after power satisfying the second duty cycle is temporally first supplied to the second heater 14, power may be supplied to the first heater 13.

As described above, the controller 12 may control power to be transmitted to the first heater 13 and the second heater 14 at different times such that power may be stably supplied from the battery 11 having a limited capacity to the first heater 13 and the second heater 14. Also, power satisfying the second duty cycle may be supplied to the second heater 14 such that the cartridge 15 may be heated according to a temperature profile of the second heater 14 and an amount of aerosol desired by the user may be provided. Also, power which is insufficiently supplied to the first heater 13 in a current control period may be compensated for in subsequent control modes such that the cigarette 2 may be heated according to a temperature profile of the first heater 13.

The method described above may be written in a program that may be executed on a computer and may be implemented in a general-purpose digital computer that operates the program by using a computer-readable recording medium. Also, a structure of data used in the method described above may be recorded on the computer-readable recording medium through various elements. Examples of the computer-readable recording medium include storage media such as magnetic storage media (e.g., ROM, RAM, USB, floppy disks, hard disks, and the like) and optical reading media (e.g., CD-ROM, DVD, and the like).

Those of ordinary skill in the art related to the present embodiments may understand that various changes in form and details can be made therein without departing from the scope of the characteristics described above. The disclosed methods should be considered in a descriptive sense only and not for purposes of limitation. The scope of the present disclosure is defined by the appended claims rather than by the foregoing description, and all differences within the equivalent range should be construed as being included in the present disclosure.

What is claimed is:

1. An aerosol generating device comprising:
   a battery;
   a first heater configured to heat a first aerosol generating substrate;
   a second heater configured to heat a second aerosol generating substrate; and
   a controller configured to control power to be supplied from the battery to the first heater and the second heater at different times,
   wherein the controller is further configured to:
   acquire a first duty cycle which is a duty cycle of power needed by the first heater in a current control period, and a second duty cycle which is a duty cycle of power needed by the second heater in the current control period,
   if a sum of the first duty cycle and the second duty cycle exceeds 100%, control the power supplied from the battery to satisfy one of the first duty cycle and the second duty cycle according to a current control mode among a plurality of control modes of the controller.

2. The aerosol generating device of claim 1, wherein the plurality of control modes comprise:
   a first control mode for controlling power to satisfy the first duty cycle for the first heater; and
   a second control mode for controlling power to satisfy the second duty cycle for the second heater.

3. The aerosol generating device of claim 1, wherein the current control mode is determined by a user command.

4. The aerosol generating device of claim 3, further comprising a communicator configured to perform communication with an external device,
   wherein the user command is input to the external device and received from the external device through the communicator.

5. The aerosol generating device of claim 1, wherein
   the controller controls power satisfying the first duty cycle to be supplied from the battery to the first heater during a first period in the current control period, and
   the controller controls power to be supplied from the battery to the second heater during at least some of a remaining period in the current control period.

6. The aerosol generating device of claim 1, wherein
   the controller controls power satisfying the second duty cycle to be supplied from the battery to the second heater during a second period in the current control period, and
   the controller controls power to be supplied from the battery to the first heater during at least some of a remaining period in the current control period.

7. The aerosol generating device of claim 6, wherein the controller controls power supplied from the battery to the first heater in the current control period and at least one subsequent control period such that a total amount of power supplied from the battery to the first heater satisfies the first duty cycle.

8. The aerosol generating device of claim 1, wherein the controller outputs a pulse width modulation signal to control power supplied from the battery to the first heater and the second heater.

9. The aerosol generating device of claim 1, wherein
   the first aerosol generating substrate is a solid substrate comprising nicotine, and
   the second aerosol generating substrate is a liquid substrate comprising an aerosol forming substance.

10. A method of controlling an aerosol generating device, the method comprising:
    acquiring a first duty cycle, which is a duty cycle of power needed by a first heater included in the aerosol generating device, and a second duty cycle, which is a duty cycle of power needed by a second heater included in the aerosol generating device;
    checking a current control mode among a plurality of control modes for controlling power supplied to the first heater and the second heater; and
    controlling power supplied from a battery to the first heater and the second heater at different times according to the checked control mode,
    wherein the controlling of the power comprises, if a sum of the first duty cycle and the second duty cycle exceeds 100%, controlling the power supplied from the battery to satisfy one of the first duty cycle and the second duty cycle according to the current control mode of the controller.

11. The method of claim 10, wherein the plurality of control modes comprises:
    a first control mode for controlling power to satisfy the first duty cycle for the first heater; and
    a second control mode for controlling power to satisfy the second duty cycle for the second heater.

12. A non-transitory recording medium recording thereon a program for executing the method of claim 10 on a computer.

* * * * *